United States Patent [19]
Ghostine et al.

[11] Patent Number: 5,191,285
[45] Date of Patent: Mar. 2, 1993

[54] SPEED RESPONSIVE FILTERING CONTROL SYSTEM FOR FLAW DETECTION APPARATUS

[75] Inventors: Said Ghostine; Paul J. Bebick, both of Bronx, N.Y.

[73] Assignee: Magnetic Analysis Corporation, Mount Vernon, N.Y.

[21] Appl. No.: 732,826

[22] Filed: Jul. 19, 1991

[51] Int. Cl.$^5$ .................... G01N 27/82; G01N 27/90; G01R 33/12
[52] U.S. Cl. .................................. 324/225; 324/226; 324/238; 324/241; 328/167
[58] Field of Search ............... 324/225, 226, 227, 233, 324/237, 238, 240, 241, 242; 328/167; 73/159, 160

[56] References Cited

U.S. PATENT DOCUMENTS

| | | | |
|---|---|---|---|
| 2,881,386 | 4/1959 | Price et al. ........................ | 324/225 |
| 3,714,558 | 1/1973 | Swanepoel ........................ | 324/225 |
| 3,835,374 | 9/1974 | Frost ............................... | 324/225 X |
| 4,330,748 | 5/1982 | Holden ............................ | 324/220 X |
| 4,380,734 | 4/1983 | Allerton .......................... | 324/225 |

*Primary Examiner*—Gerard R. Strecker
*Attorney, Agent, or Firm*—Robin, Blecker, Daley & Driscoll

[57] ABSTRACT

A system for processing signals produced by magnetic flaw detection apparatus having facility for examining objects in the course of transport thereof at speeds varying from a prescribed slow speed to a prescribed high speed, with transport frequency thus being within a first frequency range. The system comprises first circuitry for detecting the speed of transport of an object under examination and generating output signals indicative of the detected speed and extending over a given characteristic range correspondingly with the first frequency range. Second circuitry is provided for receiving the first circuitry output signals and transforming the same into a second frequency range substantially expanded as compared to the first frequency range. The second circuitry stores a plurality of band pass filter center frequency selections in the second frequency range correlated with the transport speed indications in the first circuitry output signals and is operable for providing control signals indicative of center frequency selections. Variably settable filter circuitry receives the second circuitry control signals and is responsive thereto to establish a band pass filter center frequency, applicable for the current product transport speed, for processing the signals produced by the magnetic flaw detection apparatus.

21 Claims, 4 Drawing Sheets

SPEED RESPONSIVE FILTERING CONTROL SYSTEM FOR FLAW DETECTION APPARATUS

FIELD OF THE INVENTION

This invention relates generally to nondestructive object testing for the detection of object flaws and pertains more particularly to the control of filtering in magnetic flaw detection apparatus to enhance signal-to-noise ratios, thereby to improve the accuracy of flaw detection.

BACKGROUND OF THE INVENTION

A frequently-encountered object evaluation arises in the course of drawing operations or uncoiling of stock for final cutting and finishing.

In the course of such drawing or uncoiling, need exists for performing a "last chance" eddy current nondestructive testing (NDT) inspection for short defects by what is termed the encircling coil method, i.e., wherein a detection coil fully encircles the transported stock. The test method relies on either a set of high pass or band pass filters to maximize the signal-to-noise ratio of the apparatus output signal for any flaws encountered and the method is extremely speed sensitive.

Since final automatic sorting or grading decisions are made primarily on the basis of output amplitude sensitive threshold levels, a given defect indication must yield a fairly constant output amplitude and signal-to-noise ratio and difficulties accordingly attend the situation at hand. Thus, in the type of operations under discussion, the line speed is variable, alternately stopping or slowing and then accelerating rapidly to some maximum speed to complete the cycle.

It is well-known in eddy current NDT practices, where line speed is constant, to provide a plurality of filters appropriate for different constant speeds and for the operator to select the applicable filter by manual input to the apparatus. As speed varies, however, the selected filter becomes inadequate since the output amplitude and the signal-to-noise ratio vary excessively as the object traverses the test coil at different speeds.

Efforts have been also been addressed to automated change of filters responsively to the sensing of product transport speed, but those known to applicants herein simply endeavor to correlate speed change with filter choice over filters available in quite limited number, with the result that filter shifting is a discontinuous or step-like change, yielding less than optimal accuracy in fault detection.

SUMMARY OF THE INVENTION

The present invention has as its primary object the provision of improved control of filtering in NDT practices.

A more particular object of the invention is to provide for speed-responsive filtering control, for variable product transport speed NDT apparatus which effects a substantially continuous, step-free and optimal filtering of output signals of such apparatus.

In the efficient attainment of these and other objects, the invention provides a system for processing signals produced by magnetic flaw detection apparatus having facility for examining objects in the course of transport thereof at speeds varying from a prescribed slow speed to a prescribed high speed, with transport frequency thus being within a first frequency range.

The system comprises first means for detecting the speed of transport of an object under examination and generating output signals indicative of the detected speed and extending over a given characteristic range correspondingly with the first frequency range.

Second means are provided for receiving the first means output signals and transforming the same into a second frequency range substantially expanded as compared to the first frequency range. The second means stores a plurality of band pass filter center frequency selections in the second frequency range correlated with the transport speed indications in the first means output signals and is operable for providing control signals indicative of center frequency selections.

Variably settable filter means receives the second means control signals and is responsive thereto to establish a band pass filter center frequency, applicable for the current product transport speed, for processing the signals produced by the magnetic flaw detection apparatus.

The stored center frequency selections are provided in number and spacing selected in manner effecting the above-discussed substantially continuous, step-free and optimal filtering of output signals of the NDT apparatus.

In the preferred embodiment of the system of the invention, the first means generates its output signals to have the speed-indicative characteristics as d-c voltage levels corresponding to the first frequency range. The second means includes a d-c voltage level to frequency converting means, the frequencies thereby generated extending over the second frequency range.

In one implementation of the invention, the first means includes encoder means operably associated with the transport of the object to generate pulses in the first frequency range as the first means output signals. The encoder means includes an encoder operably associated with the transport of the object which may generate pulses of frequency which may be outside of the first frequency range and has further means for down-converting the encoder generated pulses to the first frequency range. A d-c voltage is provided having a level according with the down-converted pulse frequency.

In a second implementation, the first means comprises tachometer means operably associated with the transport of the object to generate the first means output signals to have the speed-indicative characteristics as d-c voltage levels corresponding to the first frequency range.

The encoder means and the tachometer means may be jointly provided, with switching means afforded for user selection of either as the operative first means. The above-discussed manual selection of filtering for constant speed object transport may likewise be included in the system of the invention and implemented as an alternative to the first means through the switching means where constant product transport speeds are at hand.

A further object of the invention, namely, to provide gain constancy over the full second frequency range, is attained by gain control means hereinafter discussed in detail.

The foregoing and other objects and features of the invention will be further understood from the following detailed description of the preferred embodiments thereof and from the drawings wherein like reference numerals identify like components and parts throughout.

DETAILED DESCRIPTION OF PREFERRED EMBODIMENTS AND PRACTICES

Figure 1:
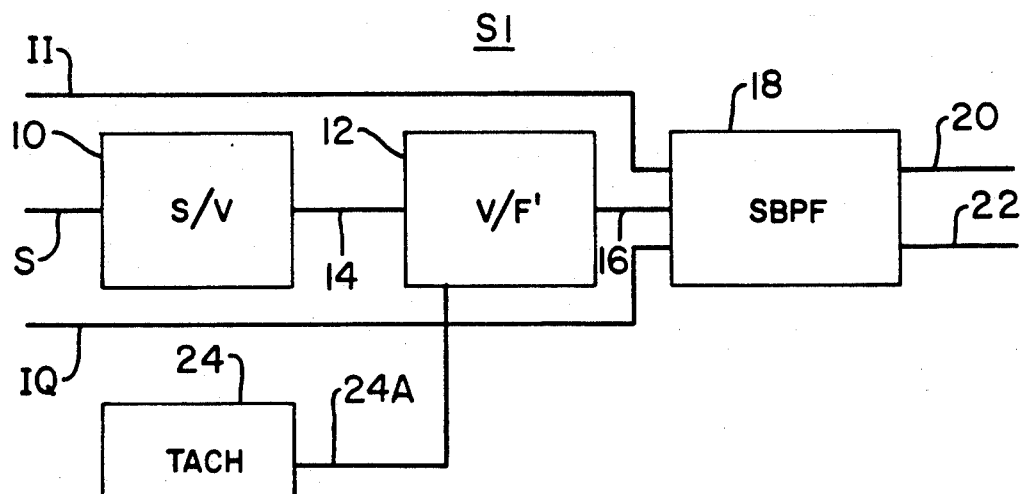
FIG. 1 is a general block diagram of the filter control system of the invention.

Referring to FIG. 1, system S1 of the invention is responsive to a product transport speed input, indicated as by the rotation of a shaft S, to effect filtering of input signals provided as outputs of an affiliated NDT system.

Typical product transport speed has an upper limit of about two thousand feet per minute and a lower limit of as low as zero (stopped) and, in variable transport speed systems, product transport speed may increasingly vary throughout such range. Hereinafter, this range and signals arising in connection therewith for processing are identified as being in a first frequency range.

Speed/Voltage converter (S/V) 10 is operative to convert input frequencies in the first frequency range into output signals having a characteristic, e.g., d-c voltage level, corresponding to the input first frequency range frequencies. By way of example, with input speed varying from zero to two thousand feet per minute, output line 14 d-c voltage level varies from zero to five volts as the first frequency range is traversed.

Voltage/frequency (V/F') converter 12 stores a plurality of bandpass filter center frequency selections in a second frequency range, as by way of a lookup table wherein the parameter cross-correlated with each stored center frequency selection is a discrete d-c voltage level indication within the range of the first frequency as provided by converter 12. In contrast to the afore-mentioned automated prior art arrangement, which offered only several center frequency selections over the speed range, converter 12 affords some one hundred and eighty or more such center frequency selections.

Converter 12 supplies its current center frequency selection over line 16 as one input to settable bandpass filter 18, second inputs to which are the outputs II and IQ (in-phase and quadrature) of the associated NDT system which are to be filtered. As variations occur in the first frequency, attending variation in product transport speed, the NDT outputs are accordingly optimally filtered by filter 18, which responds to the line 16 input to provide bandpass filters having their center frequency in correspondence with the line 16 selection, which constitutes a control signal. The filtered output signals are provided on lines 20 and 22.

The embodiment of the invention discussed to this juncture employs a speed sensor which provides an output frequency, such as an optical encoder mountable on a drive shaft of the product transport mechanism or to a wheel riding on the product, providing several pulses per revolution. The described embodiment thus has need for conversion of frequency of pulses to a d-c voltage level. Alternatively, the invention may employ a speed sensor which directly furnishes a d-c voltage level output, such as a tachometer. This alternative permits omission of frequency-to-voltage conversion and is shown in FIG. 1, wherein tachometer (TACH) 24 furnishes its output d-c voltage level on line 24A as an input to converter 12.

Figure 2:
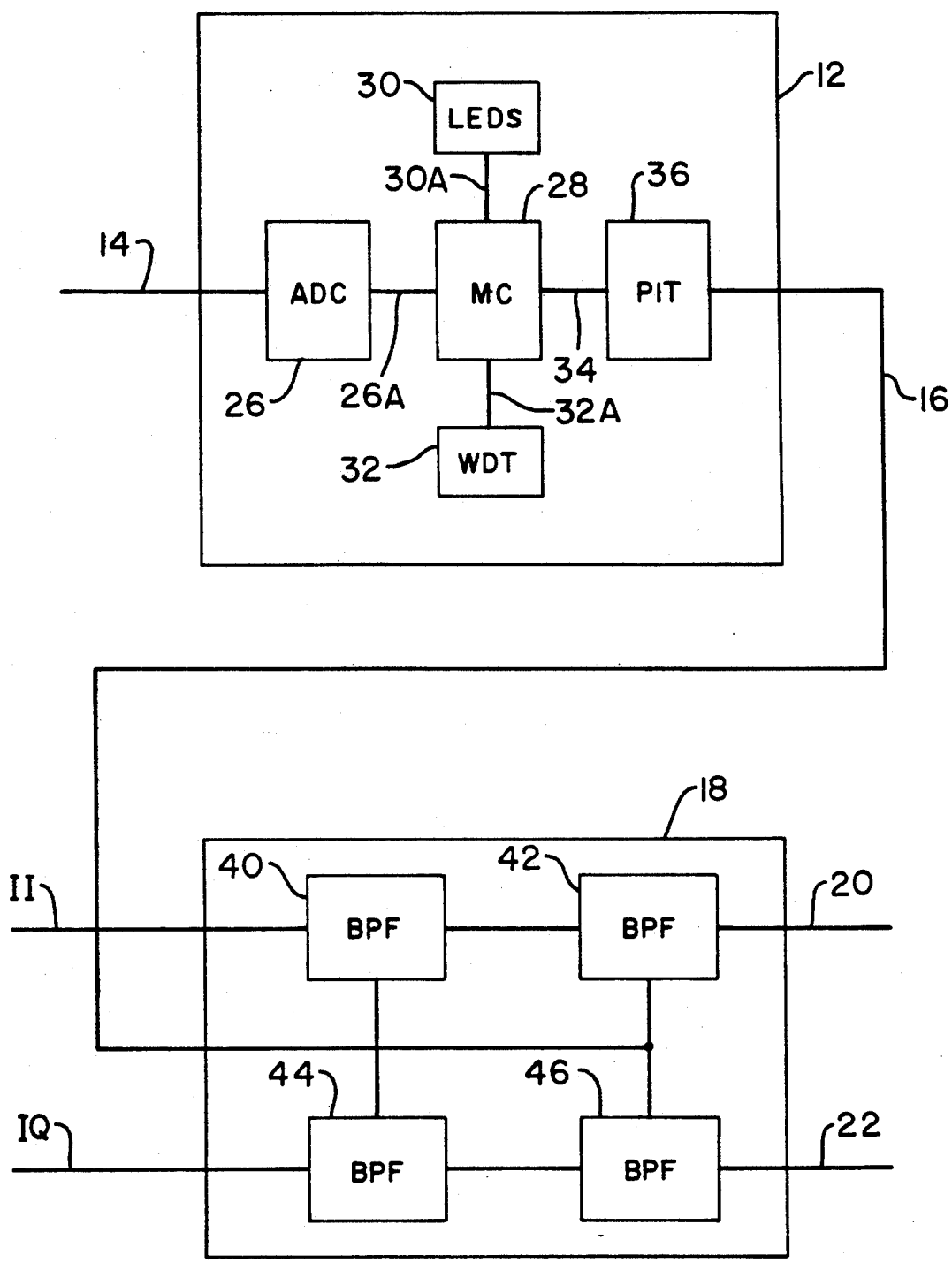
FIG. 2 is a more detailed block diagram, showing an implementation of converter 12 and settable band pass filter 18 of the FIG. 1 system.

Converter 12 and filter 18 are preferably realized in manner shown in FIG. 2. The first frequency range d-c voltage indication on line 14 is analog and is converted to digital by A/D converter (ADC) 26, which may be an eight-bit integrated circuit such as an IC AD7820.

Converter 26 furnishes its eight-bit output in parallel over lines 26A to microcontroller (MC) 28, which may be an eight-bit unit, such as an IC8748. Microcontroller 28 is a "housekeeping" control unit for effecting system timing, controlling speed range indicating indicators, such as LEDs 30 over lines 30A, looking to watch dog timer (WDT) 32 over lines 32A to reset system operation where performance is not effected within a preset time, and selecting a center frequency from the above-mentioned store, responsively to the output of converter 26, and providing the center frequency selection over lines 34 to programmable interval timer (PIT) 36.

Timer 36 is responsive to the signals on lines 34 to provide an output clock on line 16 having a frequency corresponding with the eight-bit indication on lines 34. Timer 36 may be implemented by an IC 82C54.

Filter 18 may be constituted by four ICMF10CNs (BPF) as indicated by reference numerals 40, 42, 44 and 46, two such bandpass filters being in each of the channels processing the NDT system output signals. These ICs are responsive to the line 16 clock frequency to set filter 18 with the center frequency required for the current product transport speed.

Figure 3:
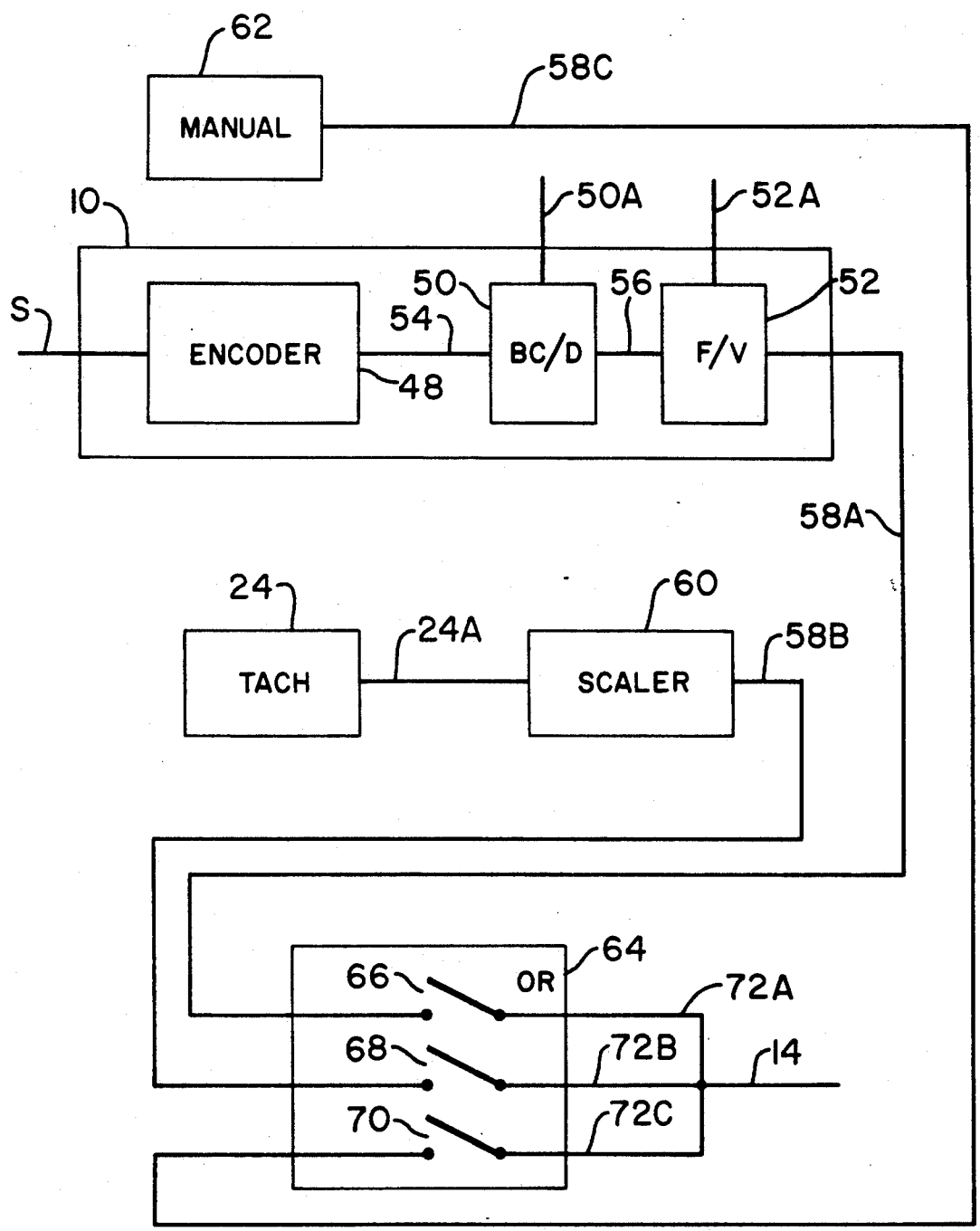
FIG. 3 illustrates a preferred arrangement of converter 10 and other units which may control line 14 of FIGS. 1 and 2.

FIG. 3 illustrates a preferred circuit arrangement of converter 10 and other units which may control line 14 of FIGS. 1 and 2. Converter 10 is realized in FIG. 3 by the aforementioned encoder wheel and sensor, identified as encoder 48, binary counter/divider (BC/D) 50 and F/V converter 52. Encoder 48 applies its output to counter/divider 50 over line 54 and the divider is operatively responsive to an input on its line 50A for purposes below discussed. The output of counter/divider 50 is furnished over line 56 to converter 52 and the converter applies its output to line 58A. Converter 52 has a control input on line 52A for purposes below discussed.

The output of tachometer 24 on line 24A is scaled in scaler 60 to correspond to the same range of d.c. level as would be the output of converter 52 if used instead, e.g., zero to five volts over the transport speed range of interest. The scaled signal is provided on line 58B.

Apparatus for use with constant transport speeds of different measures, denoted as MANUAL 62 in FIG. 3, provides a d.c. voltage level on line 58C corresponding to some value close to the selected constant transport speed.

The signals on lines 58A, 58B and 58C are applied to OR circuit 64 wherein the one of switches 66, 68 and 70 applicable to the then operative testing system is closed, conveying the control signal over one of lines 72A, 72B and 72C to line 14.

MANUAL 62 is configured to include some nine bandpass filter positions having center frequencies at octaves apart in the range of four Hertz to one thousand Hertz and selectable as by the positioning of a rotary switch (not shown) to provide d.c. voltage levels of generators connected thereto for selection.

In system setup, the product transport speed is run to its maximum, switch 70 is closed for manual mode operation and the selection of filters is varied until optimum signal-to-noise results are found for a standard product flaw.

The system is then switched to the automatic mode by closing either of switches 66 or 68 depending on whether S/V converter 10 or tachometer 24 is in use.

The input on line 50A to binary/divider 50 is set correspondingly with the nature of encoder 48, as below discussed.

While switch 68 is closed, scaler 60 is set such that the line 58B signal equates the results in the automatic mode with those in the manual mode at the product transport speed used in the manual mode. Should switch 66 be closed, the line 52A control input is set to likewise equate such automatic mode results with those set up by manual mode calibration. With either such adjustment, product transport speed can thereafter be variable with like optimum signal-to-noise results given the variable center frequency setting capacities of the invention.

Figure 4:
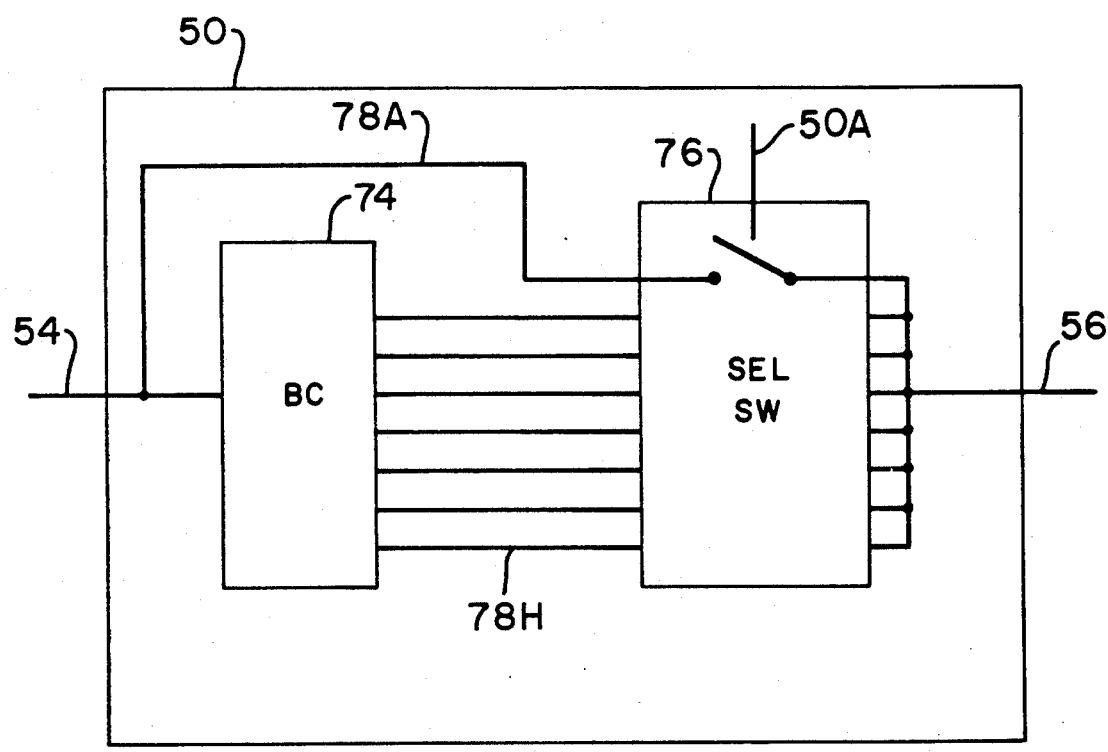
FIG. 4 is a detailed block diagram of binary counter/divider BC/D of FIG. 3.

Binary counter/divider 50 of FIG. 3 is preferably configured as is shown in FIG. 4 to include binary counter (BC) 74, which counts the encoder 48 output pulses it receives from line 54, and a selecting switch (SEL SW) 76, connected to receive the line 54 signal and the outputs of the various counting stages of counter 74 on lines 78A–78H in an eight-bit configuration. Switch 76 effects division of the count of pulses per period on line 54 based on selected closure of its eight switches as by input on line 50a, which may be a mechanical input by one setting up the system in correlation with the structure of encoder 48 and other factors below discussed. The outputs of all switches of switch 76 are connected in common to line 56 and the selected switch thus conducts its output to F/V converter 52.

Counter 74 may be constituted by an IC4040, switch 76 by a SW DIP-8 and converter 52 by an ICLM2917.

The line 52A input to converter 52 is derived from a variable d.c. voltage level source (not shown) and is applied to terminal three of the ICLM2917.

In a practical realization of encoder 48 of FIG. 3, it generates sixteen pulses per revolution of shaft S and switch 76 is set by line 50A input to select the divide-by-four output of counter 74, such that four pulses per shaft S revolution are applied to line 56 and the d.c. voltage level on line 52A is adjusted to provide for automatic/manual equivalence in performance at the selected manual mode maximum constant speed for the case in which one encoder revolution corresponds with one foot of product travel, ultimately divided down to four pulses per foot of product travel.

If encoder 48 is otherwise configured, i.e., with a smaller wheel from that giving sixteen pulses per foot of product travel, e.g., giving thirty-two pulses per foot of product travel, switch 76 is set by line 50A input to select the divide-by-eight output of counter 74, whereby the desired four pulses per foot of product travel are provided on line 56. Likewise, for an increase in the size of the encoder wheel, switch 76 is set in the other direction to again select the output of counter 74 providing the four pulses per foot of product travel.

In most extant eddy current NDT arrangements, a natural rolloff of system sensitivity occurs with progressively higher flaw signal frequencies as the product travel speed through the test coil is increased above some minimum value. This decrease in system gain for progressively higher frequencies is due to the need for a band limiting low pass filter in each channel, at approximately twelve hundred Hertz. It attenuates those higher frequencies in a gradual manner until its six decibel cutoff point, where it sharply attenuates even higher frequency detrimental electronic noise as well as the detection system's feedthrough or carrier noise generated, especially at low test frequencies.

In accordance with the subject invention the output of converter 10 or tachometer 24 is used, in addition to its above described usage, to compensate for the foregoing system deficiency, as is now discussed in connection with FIG. 5, which shows composite NDT and filter control system apparatus in accordance with the invention.

Figure 5:
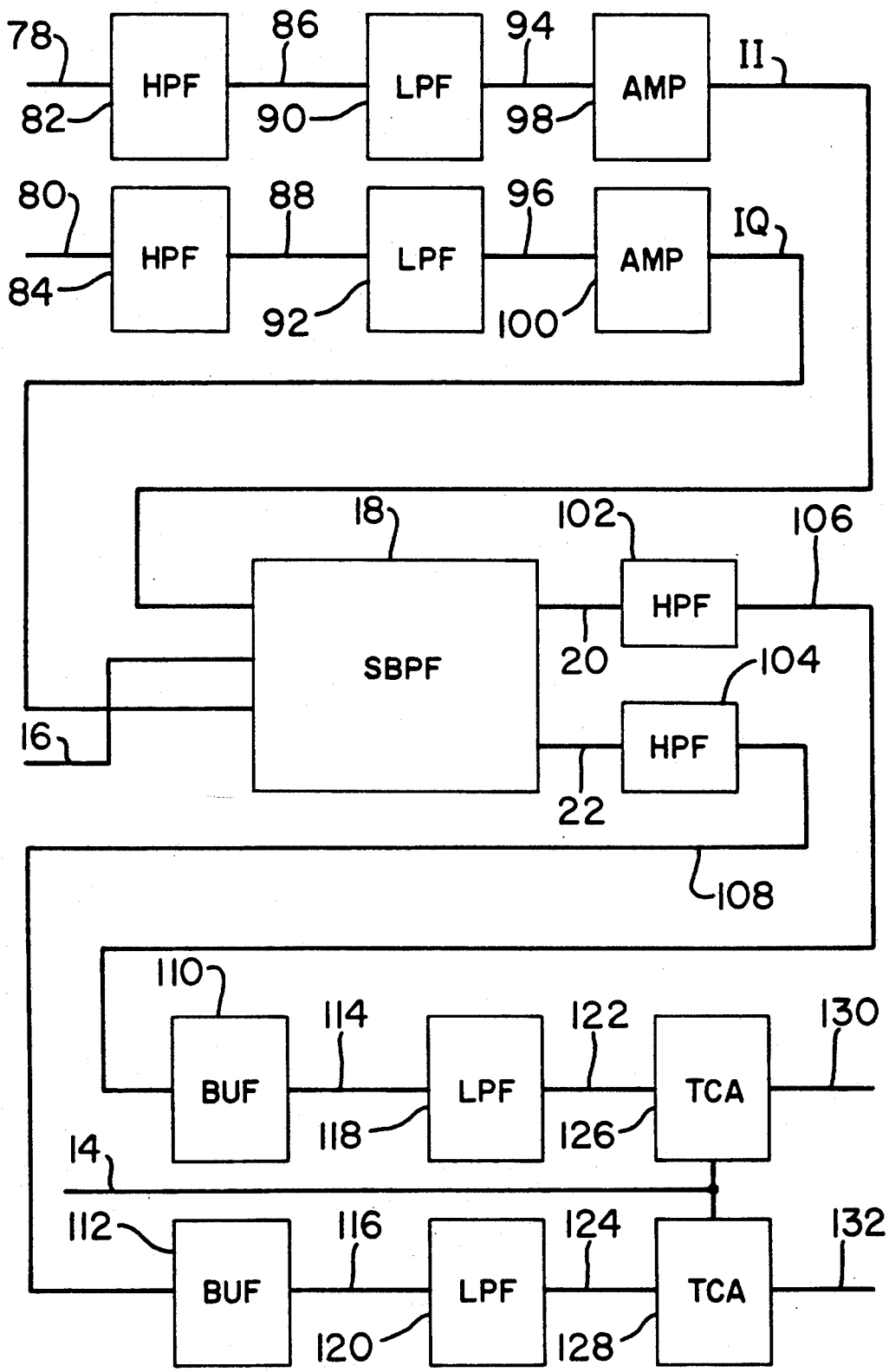
FIG. 5 shows a block diagram of composite NDT and filter control system apparatus in accordance with the invention.

In FIG. 5, NDT system flaw indicating signals are applied to lines 78 and 80 and furnished thereby to high pass filters (HPF) 82 and 84, which have quite low cutoff frequencies for the purpose of blocking d.c. content of the signals on lines 78 and 80.

Lines 86 and 88 convey the output signals of filters 82 and 84 to low pass filters (LPF) 90 and 92, which have quite high cutoff frequencies and serve to reduce the NDT system output carrier as respects noise content.

The output signals of filters 90 and 92 are conveyed by lines 94 and 96 to amplifiers (AMP) 98 and 100 whose outputs are on the aforementioned lines II and IQ and are applied with the line 16 signal output from converter 12 to settable band pass filter 18.

The output signals of SBPF 18 on lines 20 and 22, above discussed, are applied to high pass filters (HPF) 102 and 104, which have quite low cutoff frequencies and serve to block d.c. content of the line 20 and 22 signals.

Lines 106 and 108 convey the output signals of filters 102 and 104 to buffers (BUF) 110 and 112, which in turn provide signals on lines 114 and 116 to low pass filters (LPF) 118 and 120, which have quite high cutoff frequencies and serve to reduce filter 18 switching noise.

The outputs of filters 118 and 120, which yield system-filtered output signals, are provided over lines 122 and 124 to transconductance amplifiers (TCA) 126 and 128, which yield system filtered and gain-controlled output signals on lines 130 and 132.

In attaining the foregoing compensation for natural rolloff of NDT systems at the high frequency end, the invention increases the gains of amplifiers 126 and 128 in accordance with the increased d.c. level of the signal on line 14, i.e., the signal emanating from OR circuit 64.

Various changes may be introduced in the preferred embodiments of the invention above set forth and modifications may evidently be introduced in the practices described without departing from the invention. Accordingly, it is to be understood that the detailed system showings and described methods are intended in an illustrative and not in a limiting sense. The true spirit and scope of the invention is set forth in the following claims.

What is claimed is:

1. A system for processing signals produced by magnetic flaw detection apparatus having facility for examining objects in the course of transport thereof at speeds varying from a prescribed slow speed to a prescribed high speed with transport frequency thereby being within a first frequency range, said system comprising:
   (a) first means for detecting the speed of transport of an object under examination and generating output signals having characteristics indicative to said detected speed and extending over a given characteristic range correspondingly with said first frequency range;

(b) second means for receiving said first means output signals and transforming the same into a second frequency range substantially expanded as compared to said first frequency range, said second means storing a plurality of band pass filter center frequency selections in said second frequency range correlated with said transport speed indications in said first means output signals and operable for providing control signals indicative of center frequency selections corresponding with said first means output signals; and (c) variably settable filter means for receiving said signals produced by said magnetic flaw detection apparatus and said second means control signals and responsive to said second means control signals to establish a band pass filter center frequency for processing said signals received from said magnetic flaw detection apparatus.

2. The system claimed in claim 1 wherein said first means generates its output signals to have said speed-indicative characteristics as d-c voltage levels extending over said given characteristic range.

3. The system claimed in claim 2 wherein said second means comprises a d-c voltage level to frequency converting means.

4. The system claimed in claim 2 wherein said magnetic flaw detection apparatus produces first and second signals in respective mutual quadrature phase relation and wherein said variably settable filter means comprises first and second variably settable filters each receiving said second means control signals and a respective one of said first and second signals.

5. The system claimed n claim 3 further comprising manually settable means for generating output signals having d-c voltage levels selectively distributed in said given characteristic range and selectively settable to generate any one of said output signals and switch means operable to furnish either said first means output signals or said manually settable means output means to said second means.

6. The system claimed in claim 1 wherein said first means includes encoder means operably associated with the transport of said object to generate pulses in said first frequency range as said first means output signals.

7. The system claimed in claim 6 wherein said encoder means includes an encoder operably associated with the transport of said object to generate pulses of frequency outside of said first frequency range and further means for converting said encoder generated pulses to said first frequency range.

8. The system claimed in claim 1 wherein said first means comprises tachometer means operably associated with the transport of said object to generate said first means output signals to have said speed-indicative characteristics as d-c voltage levels extending over said given characteristic range.

9. The system claimed in claim 1 wherein said first means includes encoder means operably associated with the transport of said object to generate pulses in said first frequency range as said first means output signals and tachometer means operably associated with the transport of said object to generate said first means output signals to have said speed-indicative characteristics as d-c voltage levels extending over said given characteristic range, said system including switch means operable to furnish either said encoder means generated pulses or said tachometer means generated signals as said first means output signals.

10. The system claimed in claim 9 further comprising manually settable means for generating output signals having d-c voltage levels selectively distributed in said given characteristic range and selectively settable to generate any one of said output signals, said switch means being further operable to furnish said manually settable means output signals to said second means.

11. A system for processing signals produced by magnetic flaw detection apparatus having facility for examining objects in the course of transport thereof at speeds varying from a prescribed slow speed to a prescribed high speed with transport frequency thereby being within a first frequency range, said system comprising:

(a) first means for detecting the speed of transport of an object under examination and generating output signals having characteristics indicative of said detected speed and extending over a given characteristic range correspondingly with said first frequency range;

(b) second means for receiving said first means output signals and transforming the same into a second frequency range substantially expanded as compared to said first frequency range, said second means storing a plurality of band pass filter center frequency selections in said second frequency range correlated with said transport speed indications in said first means output signals and operable for providing control signals indicative of center frequency selections corresponding with said first means output signals;

(c) variably settable filter means for receiving said signals produced by said magnetic flaw detection apparatus and said second means control signals and responsive to said second means control signals to establish a band pass filter center frequency for processing said signals received from said magnetic flaw detection apparatus and outputting frequency-processed signals; and (d) third means for receiving said frequency-processed signals produced by said variably settable filter means and said first means output signals and varying the processing in said third means of said frequency-processed signals in accordance with said first means output signals.

12. The system claimed in claim 11 wherein said first means generates its output signals to have said speed-indicative characteristics as d-c voltage levels extending over said given characteristic range.

13. The system claimed in claim 11 wherein said second means comprises a d-c voltage level to frequency converting means.

14. The system claimed in claim 13 wherein said magnetic flaw detection apparatus produces first and second signals in respective mutual quadrature phase relation and wherein said variably settable filter means comprises first and second variably settable filters each receiving said second means control signals and a respective one of said first and second signals.

15. The system claimed in claim 11 further comprising manually settable means for generating output signals having d-c voltage levels selectively distributed in said given characteristic range and selectively settable to generate any one of said output signals and switch means operable to furnish either said first means output signals or said manually settable means output means to said second means.

16. The system claimed in claim 11 wherein said first means includes encoder means operably associated with the transport of said object to generate pulses in said first frequency range as said first means output signals.

17. The system claimed in claim 16 wherein said encoder means includes an encoder operably associated with the transport of said object to generate pulses of frequency outside of said first frequency range and further means for converting said encoder generated pulses to said first frequency range.

18. The system claimed in claim 11 wherein said first means comprises tachometer means operably associated with the transport of said object to generate said first means output signals to have said speed-indicative characteristics as d-c voltage levels extending over said given characteristic range.

19. The system claimed in claim 11 wherein said first means includes encoder means operably associated with the transport of said object to generate pulses in said first frequency range as said first means output signals and tachometer means operably associated with the transport of said object to generate said first means output signals to have said speed-indicative characteristics as d-c voltage levels extending over said given characteristic range, said system including switch means operable to furnish either said encoder means generated pulses or said tachometer means generated signals as said first means output signals.

20. The system claimed in claim 19 further comprising manually settable means for generating output signals having d-c voltage levels selectively distributed in said given characteristic range and selectively settable to generate any one of said output signals, said switch means being further operable to furnish said manually settable means output signals to said second means.

21. The system claimed in claim 11 wherein said third means comprises variable gain amplifier means and wherein the gain of said variable gain amplifier means is set correspondingly with a characteristic of said first means output signals.

* * * * *